(12) United States Patent
Garcia-Rodenas et al.

(10) Patent No.: US 9,144,250 B2
(45) Date of Patent: *Sep. 29, 2015

(54) NUTRITIONAL FORMULATION FOR PROMOTING CATCH-UP GROWTH

(75) Inventors: Clara Lucia Garcia-Rodenas, Forel (CH); Gabriela Bergonzelli, Bussigny-pres-Lausanne (CH)

(73) Assignee: Nestec S.A., Vevey (CH)

( * ) Notice: Subject to any disclaimer, the term of this patent is extended or adjusted under 35 U.S.C. 154(b) by 2021 days.

This patent is subject to a terminal disclaimer.

(21) Appl. No.: 12/089,423

(22) PCT Filed: Oct. 2, 2006

(86) PCT No.: PCT/EP2006/066970
§ 371 (c)(1),
(2), (4) Date: Apr. 7, 2008

(87) PCT Pub. No.: WO2007/039596
PCT Pub. Date: Apr. 12, 2007

(65) Prior Publication Data
US 2008/0254012 A1 Oct. 16, 2008

(30) Foreign Application Priority Data
Oct. 5, 2005 (EP) .................... 05109248

(51) Int. Cl.
| | | |
|---|---|---|
| A61K 31/202 | (2006.01) |
| A61K 31/702 | (2006.01) |
| A23L 1/29 | (2006.01) |
| A23L 1/30 | (2006.01) |
| A23L 1/308 | (2006.01) |
| A61K 35/747 | (2015.01) |
| A61K 45/06 | (2006.01) |

(52) U.S. Cl.
CPC .............. *A23L 1/3008* (2013.01); *A23L 1/296* (2013.01); *A23L 1/308* (2013.01); *A23L 1/3014* (2013.01); *A61K 31/202* (2013.01); *A61K 31/702* (2013.01); *A61K 35/747* (2013.01); *A61K 45/06* (2013.01); *A23V 2002/00* (2013.01); *A23Y 2220/63* (2013.01)

(58) Field of Classification Search
CPC ............ A61K 2300/00; A61K 31/715; A61K 31/202; A61K 31/702; A61K 35/747; A61K 35/745; A61K 38/1841; A61K 31/733; A61K 31/7004; A61K 31/197; A61K 31/198; A61K 31/736; A61K 38/05; A61K 31/7016; A61K 45/06; A61K 2035/115; A61K 35/744; A61K 38/16; A61K 35/741; A61K 35/74; A61K 35/742

See application file for complete search history.

(56) References Cited

U.S. PATENT DOCUMENTS

| | | | |
|---|---|---|---|
| 6,592,863 B2 * | 7/2003 | Fuchs et al. ................. | 424/93.1 |
| 8,394,370 B2 * | 3/2013 | Garcia-Rodenas et al. ......................... | 424/93.45 |
| 2003/0190363 A1 | 10/2003 | O'Connor et al. | |
| 2004/0170668 A1 | 9/2004 | Schade | |
| 2005/0153019 A1 | 7/2005 | Fuchs et al. | |

FOREIGN PATENT DOCUMENTS

| | | |
|---|---|---|
| EP | 0 904 784 | 3/1999 |
| WO | WO 2004/089115 | 10/2004 |
| WO | WO 2004/112509 | 12/2004 |
| WO | WO 2005/063050 | 7/2005 |

OTHER PUBLICATIONS

Bengmark, S. et al., "Use of Some Pre-, Pro- and Sanbiotics in Critically Ill Patient," Bailliere's Best Practice and Research, vol. 17, No. 5, pp. 833-848 (2003).
International Preliminary Report of Patentability (6 pgs.).
Fuller, S. "Probiotics in Man and Animals," Journal of Applied Bacteriology, vol. 66, pp. 365-378 (1989).
Gibson, G. et al., "Dietary Modulation of the Human Colonic Microbiota: Introducing the Concept of Prebiotics," J. Nutr., vol. 125, pp. 1401-1412 (1995).

\* cited by examiner

*Primary Examiner* — Debbie K Ware
(74) *Attorney, Agent, or Firm* — K&L Gates LLP

(57) ABSTRACT

This invention relates to a nutritional formulation comprising an n3 long-chain polyunsaturated fatty acid (LC-PUFA), a prebiotic fiber and a probiotic bacterial strain which ingredients act together in a synergistic fashion to promote catch-up growth in young mammals whose growth has been retarded because the young mammal has been subjected to physical or mental stress.

19 Claims, 5 Drawing Sheets

US 9,144,250 B2

NUTRITIONAL FORMULATION FOR PROMOTING CATCH-UP GROWTH

FIELD OF THE INVENTION

The present invention relates to formulations to promote catch up growth in young mammals whose growth has been retarded because the young mammal has been subjected to physical or mental stress and to the use of such formulations. In particular, the present invention relates to a formulation containing a synergistic combination of ingredients to promote catch up growth.

BACKGROUND OF THE INVENTION

It has been recognised for many years that the growth pattern of young mammals who suffer stress whether as a result of physical illness or injury or psychological trauma is often interrupted. If the young mammal makes a swift recovery and adequate nutrition is available, it may then compensate for the growth which should have taken place during the period of stress and this sudden spurt of growth is known as "catch up growth". However, this does not always happen. For example, the young mammal may suffer from anorexia both during the illness or trauma and in its immediate aftermath and food intake may therefore be limited. In severe cases it may be that the animal never attains the physical stature that it would have reached had the stress not been suffered.

This phenomenon may be seen in young mammals including humans from infancy throughout the period in their lives during which they are still growing. Although it is desirable to ensure that reduced growth during periods of physical or mental stress is compensated, it is also important that catch up growth should not be excessive as there are indications that periods of very rapid and/or very extensive catch up growth particularly during infancy may be linked with a risk of future obesity.

Therefore, an object of the present invention is to provide a formulation suitable to promote optimal catch up growth in young mammals which have been subject to physical or mental stress.

SUMMARY OF THE INVENTION

During the studies leading to the present invention the present inventors unexpectedly observed that administration of a specific combination of ingredients promoted catch-up growth in young mammals who had been subjected to stress.

Accordingly, in a first aspect, the present invention provides a nutritional formulation for promoting catch-up growth comprising a source of lipids containing fatty acids, an n3 long-chain polyunsaturated fatty acid (LC-PUFA) present in an amount of at least 0.01% of the fatty acids in the composition, a prebiotic fibre in an amount of at least 0.001 g/g of formulation and a probiotic bacterial strain in an amount of from $10^3$-$10^{11}$ cfu/g of formulation.

In a second aspect, the present invention provides the use of an n3 long-chain polyunsaturated fatty acid (LC-PUFA), a prebiotic fibre and a probiotic bacterial strain for the manufacture of a nutritional formulation or medicament for the promotion of catch-up growth in sick and convalescent young mammals.

The present invention further provides a method of promoting catch up growth in a sick or convalescent young mammal which comprises administering a therapeutic amount of a formulation comprising an n3 LC-PUFA, a prebiotic fibre and a probiotic bacterial strain to a young mammal in need thereof.

An advantage of the present invention is that it provides a possibility to promote catch up growth without administration of synthetic hormones but using a synergistic combination of food grade ingredients. Further, young mammals under stress frequently suffer from anorexia and are unwilling or unable to consume large quantities of calories; an advantage of the present invention is that it offers the opportunity to promote catch up growth without increasing the caloric intake, with equilibrated lean and fat body mass and without promoting obesity.

DETAILED DESCRIPTION OF THE INVENTION

Figure 1:
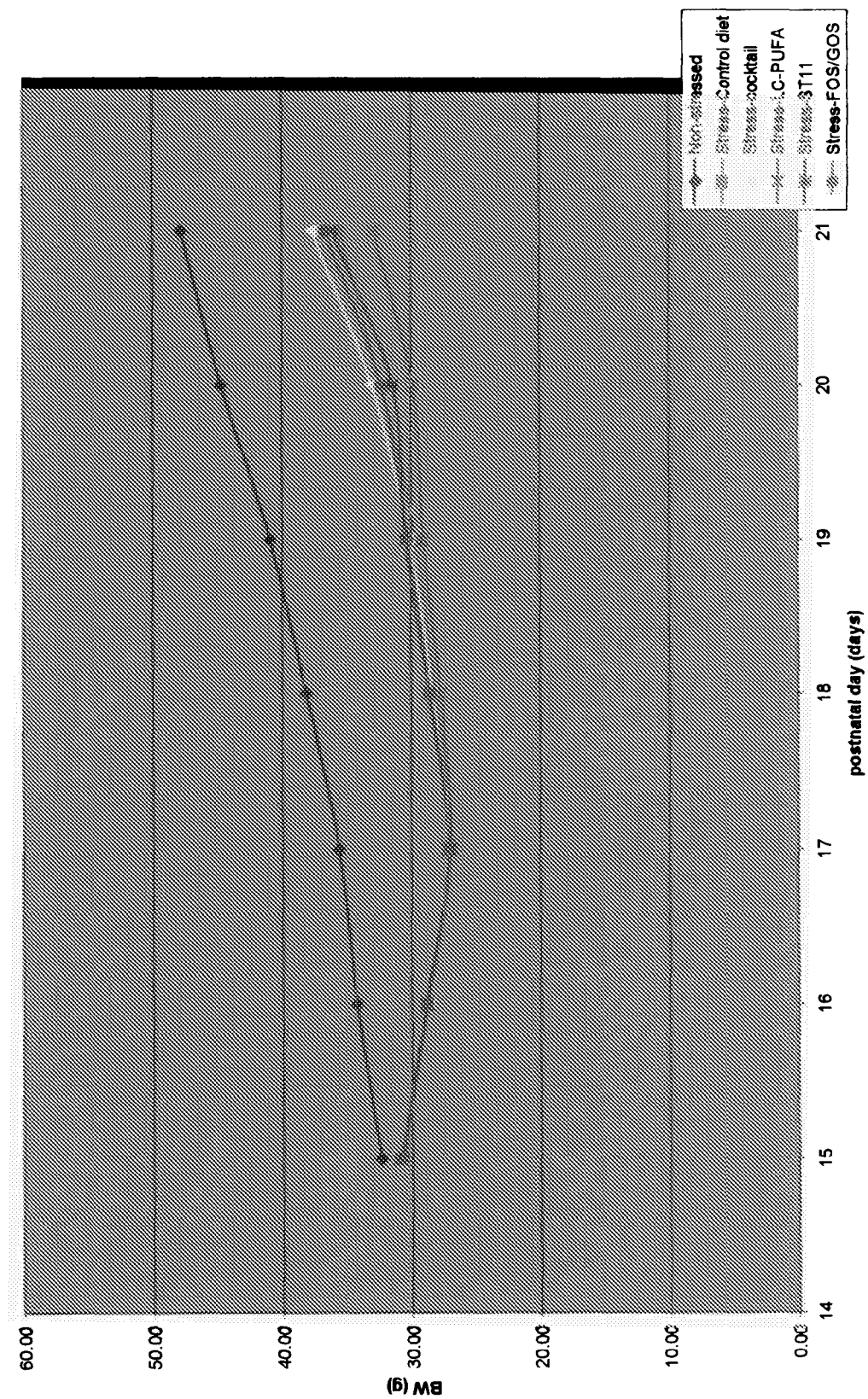
FIG. 1 shows the evolution of the body weight of 6 groups of rats receiving different diets from post-natal day (PND) 15-21

In this specification, the following terms have the meanings assigned to them below:—

"probiotic bacterial strain" means a live microbial feed supplement which beneficially affects the host animal by improving its intestinal microbial balance (from "Probiotics in Man and Animals", J. Appl Bacteriol. 66: 365-378, 1989)

"prebiotic" means a non-digestible food ingredient that beneficially affects the host by selectively stimulating the growth and/or activity of one or a limited number of bacteria in the colon and thus improves host health (from "Dietary Modulation of the Human Colonic Microbiota: Introducing the Concept of Prebiotics", J. Nutr. 125: 1401-1412, 1995)

"young mammal" means any mammal including humans and companion animals from birth to the age at which a mammal of the species concerned attains its full physical stature.

Preferably the probiotic bacterial strain is a *Lactobacillus* or *Bifidobacterium* strain. Suitable *Lactobacillus* strains include *Lactobacillus rhamnosus* ATCC 53103 obtainable from Valio OY, Finland and *Lactobacillus paracasei* CNCM I-2116 with the latter being particularly preferred. Suitable *Bifidobacterium* strains include *Bifidobacterium longum* BB536 obtainable from Morinaga, Japan, the strain of *Bifidobacterium lactis* obtainable from Christian Hansen of Denmark under the trade mark Bb12 and *Bifidobacterium lactis* CNCM I-3446. Combinations of strains may be used with combinations of a *Lactobacillus* and a *Bifidobacterium* being particularly preferred. The selected strain or strains may be included in the formulation in the form of a powder obtained by freeze- or spray-drying. Alternatively, the nutritional formulation may additionally comprise a fermentable foodstuff such as milk or cereals and the probiotic bacterial strain may be used to ferment the foodstuff.

The prebiotic fibre may be selected from fructo-oligosaccharides, galacto-oligosaccharides, sialo-oligosaccharides, xylo-oligosaccharides, inulin, arabic gum, guar gum, resistant starch, milk-derived oligosaccharides and mixtures thereof. Preferred prebiotic fibres are fructo-oligosaccharides, inulin, gum Arabic and galacto-oligosaccharides, particularly mixtures of from 70 to 95% galacto-oligosaccharide and 30 to 5% fructo-oligosaccharide and 40 to 60% gum Arabic, 30 to 40% fructo-oligosaccharide and 10 to 20% inulin. A suitable galacto-oligosaccharide is that sold by Borculo Domo Ingredients under the trade mark Vivinal GOS 10. A suitable fructo-oligosaccharide is that sold by Orafti S.A under the trade mark Raftilose P95. A suitable inulin is that sold by Orafti S.A under the trade mark Raftiline HP. A suitable gum Arabic is that sold by CNI under the trade mark FiberGum P. Preferably, the prebiotic fibre or fibres is/are present in a total amount of from 0.02-0.05 g/g of formulation.

The formulation contains at least one n-3 LC-PUFA such as a C20 or C22 n-3 fatty acid. The C20 or C22 n-3 LC-PUFA is preferably present in an amount of at least 0.1% by weight of all fatty acids in the formulation. Preferably, the n-3 LC-PUFA is docosahexanoic acid (DHA, C22:6, n-3).

Preferably, the formulation also contains an n-6 polyunsaturated fatty acid such as a C20 or C22 n-6 fatty acid. A suitable n-6 LC-PUFA is arachidonic acid (AA, C20:4 n-6). The C20 or C22 n-6 LC-PUFA is preferably present in an amount of at least 0.1% by weight of all fatty acids in the formulation.

The n6:n3 ratio is preferably between 1:2 to 8:1, more preferably between 4:1 to 8:1. The source of the LC-PUFA may be, for example, egg lipids, fungal oil, low EPA fish oil or algal oil.

The formulation may take the form of a nutritional supplement or it may provide complete nutrition. Examples of suitable bases for a nutritional formulation according to the present invention are milk, yoghurt, curd, cheese, fermented milks and milk products, fermented cereal based products, milk based powders, infant formulae and compositions for oral and tube feeding.

In a preferred embodiment, the present invention provides an infant formula or a paediatric nutritional formulation. Apart from the synergistic combination of ingredients described above it may comprise a protein source and/or a carbohydrate source.

The source of protein may be any suitable dietary protein; for example animal proteins (such as milk proteins, meat proteins, egg proteins), vegetable proteins (such as soy, wheat, rice or pea proteins), mixtures of free amino acids, or combination thereof. Milk proteins such as casein and whey are particularly preferred. In a preferred embodiment of a paediatric formulation, the protein source provides from 7 to 14% of the energy of the composition.

For a paediatric formulation, the lipid source preferably provides from 30% to 50% of the energy of the formulation. The lipids making up the lipid source may be any suitable fat or fat mixture. Vegetable fats are particularly suitable; for example soy oil, palm oil, coconut oil, safflower oil, sunflower oil, corn oil, canola oil, lecithins, and the like. Animal fats such as milk fats may also be added if desired. Preferably, the fat source includes at least 15% medium chain triglycerides and the fatty acid profile lies in the range 20 to 40% saturated fatty acids, 45 to 60% monounsaturated fatty acids and 10 to 25% polyunsaturated fatty acids.

If the paediatric formulation includes a carbohydrate source, the carbohydrate source preferably provides from 40% to 60% of the energy of the formulation. Any suitable carbohydrate or mixture of carbohydrates may be used, for example sucrose, lactose, glucose, fructose, corn syrup solids and maltodextrins.

Suitable vitamins and minerals may be included in the formulation in the usual manner to meet the appropriate guidelines. One or more food grade emulsifiers may be incorporated into the formulation if desired, for example diacetyl-tartaric acid esters of mono-diglycerides, lecithin and mono- and di-glycerides. Similarly suitable salts and stabilisers may be included.

The formulation is preferably enterally administrable for example in the form of a powder for reconstitution with water. The reconstituted formulation may be administered orally or by naso-gastric tube. It may be prepared in any suitable manner, for example, by blending together the source of dietary protein, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water that has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenized; for example in two stages.

The liquid mixture may then be thermally treated to reduce bacterial loads. For example, the liquid mixture may be rapidly heated to a temperature in the range of about 80° C. to about 150° C. for about 5 seconds to about 5 minutes. This may be carried out by steam injection, autoclave or by heat exchanger; for example a plate heat exchanger. The liquid mixture may then be cooled to about 60° C. to about 85° C.; for example by flash cooling. The liquid mixture may then be again homogenized; for example in two stages at about 7 MPa to about 40 MPa in the first stage and about 2 MPa to about 14 MPa in the second stage. The homogenized mixture may then be further cooled to add any heat sensitive components; such as vitamins and minerals. The pH and solids content of the homogenized mixture is conveniently standardized at this point.

The homogenized mixture is transferred to a suitable drying apparatus such as a spray drier or freeze drier and converted to powder. The powder should have a moisture content of less than about 5% by weight. The probiotic bacterial strain may conveniently be added at this point by dry-mixing.

If it is desired to produce a liquid formulation, the homogenized mixture is preferably aseptically filled into suitable containers. Aseptic filling of the containers may be carried out by pre-heating the homogenized mixture (for example to about 75 to 85° C.) and then injecting steam into the homogenized mixture to raise the temperature to about 140 to 160° C.; for example at about 150° C. The homogenized mixture may then be cooled, for example by flash cooling, to a temperature of about 75 to 85° C. The homogenized mixture may then be homogenized, further cooled to about room temperature and filled into containers. Suitable apparatus for carrying out aseptic filling of this nature is commercially available. The liquid formula may be in the form of a ready to feed formula having a solids content of about 10 to about 14% by weight or may be in the form of a concentrate; usually of solids content of about 20 to about 26% by weight. Flavours may be added to the liquid formulas. In the case of liquid formulas, the probiotic bacterial strain is preferably supplied packed separately for admixture immediately before consumption of the liquid formulation.

The amount of the formulation required to be fed to the young mammal will vary depending upon factors such as the patient's condition, body weight, and age, and whether the formulation is the sole source of nutrition. In general, sufficient of the formulation is administered to provide the patient with between 1 and 4 g protein per kg of body weight per day supplemented with the ingredients according to the present invention in the amounts as indicated above. If the nutritional formulation is used as a supplement to other foods, the amount of the nutritional formulation that is administered daily may be decreased accordingly.

The following non-limiting examples further illustrate the invention.

EXAMPLE 1

An example of the composition of a paediatric nutritional formulation according to the present invention is given below. This composition is given by way of illustration only.

The formula has the following composition (per 100 g of powder): total fat 18.3 g, total protein 13.9 g, total carbohydrates 59.2 g, AA enriched oil (fungal) 0.2 g, DHA enriched oil (Low EPA fish oil) 0.2 g, gum Arabic/FOS/inulin (51%/34%/15%) 12 g, *L. paracasei* CNCM I-2116 (Nestle, spray-dried powder, 10E12 cfu/g) 0.1 g, *B. longum* BB536 (Morinaga, spray-dried powder, 5×10E12 cfu/g) 0.1 g, Sodium 222 mg, Potassium 500 mg, Chloride 370 mg, Phosphorus 278 mg, Calcium 417 mg, Magnesium 53 mg, Manganese 231 µg, Vitamin A 680 IU, Vitamin D 180 IU, Vitamin E 6.8 IU, Vitamin C 36 mg, Vitamin K1 18 µg, Vitamin B1 0.27 mg, Vitamin B2 0.36 mg, Vitamin B6 0.36 mg, Niacin 2.7 mg, Folic acid 91 µg, Pantothenic acid 1.4 mg, Vitamin B12 0.68 µg, Biotin 6.8 µg, Choline 110 mg, Taurine 36 mg, Carnitine 18 mg, Iron 4.5 mg, Iodine 36 µg, Copper 0.36 mg and Zinc 4.5 mg.

The formula is reconstituted by mixing 221 g of powder with 779 ml of water to give 1 L of ready-to-drink preparation. The composition given above can vary to accommodate national directives concerning the amounts of specific ingredients. Other trace elements (e.g. selenium, chromium, molybdenum, fluoride) may be added in adequate amount according to age.

EXAMPLE 2

The following experiments demonstrate the effect on stressed neonatal rats of feeding with a nutritional formulation according to the invention, nutritional formulations supplemented with the individual components of the composition according to the invention and an unsupplemented nutritional formulation.

Animals

Primiparous time-pregnant female Long-Evans Hooded rats were purchased from Janvier (France), arriving at the animal care facility on gestational days 10 and 11. They were individually housed until delivery under constant temperature and humidity, and maintained on a 12:12 dark:light cycle. Food and water were provided ad libitum. Housing conditions were maintained for the duration of the protocol. One day after delivery (postnatal day 2—PND2), dams were removed from their maternity cages and the sex of the pups was determined. Standardized litters of 8 male pups were randomly assigned for fostering.

Neonatal Stress

The dams and their pups were assigned to one of two rearing conditions: 1) maternal separation groups, exposed to a 180 min period of daily maternal separation on PND 2 to 14 (MS), or 2) handled controls, exposed to daily manipulation (weighing and 15 min handling) but not to maternal separation (NS). At 9 am, the dams were removed from their home cage and kept in waiting cages throughout the 3 hrs separation period (MS dams) or 15 min handling period (NS dams). Each MS litter was removed from the nest, weighed, and placed as a group in an isolation cage in an adjacent room. The isolation cages were kept at 32.0±0.5° C. At the end of the separation period pups were returned to their home cage and rolled in the soiled bedding before reuniting them with their foster mother. Litters from the NS groups were treated similarly but instead the 3 hours separation period, they were gently handled for 15 min. There were 5 groups of MS pups and 1 group of NS pups, each group consisting of 8 pups.

Fifty percent of the soiled bedding of the home cage was replaced with clean bedding once a week.

Experimental Protocol

All pups in the 5 MS groups were separated completely from their foster mothers at PND 15 and weaned onto the control diet or one of the supplemented diets 1 to 4. The pups from each of these groups were housed together (5 animals/cage). The NS group remained with their mothers until PND 21. From PND 15 to 21 the weight of all pups was monitored daily. At PND 21, the pups from the NS group were weaned onto the control diet. From then until the end of the study at PND 36, all pups were individually housed. From PND 15 to PND 36, pups in the MS group continued to receive the diet onto which they had been weaned. Food was replaced by a fresh batch every morning and all pups received their diet ad libitum Diets Animals in the MS groups were fed from PND15 till PND 36 with nutritionally adapted semisynthetic diets (modified AIN 93 G) whose compositions are shown in Table 1 below. Supplemented diets contained one or more of the following functional ingredients: *Lactobacillus paracasei* CNCM I-2116 ($4 \times 10^{10}$ cfu in 0.8 ml of spent culture medium/100 g diet); 0.4 g/100 g diet inulin (Raftiline HP®, Orafti SA, Belgium), 3.6 g/100 g diet GOS (Vivinal® GOS 10, Borculo Domo Ingredients, The Netherlands), 2 g/100 g diet arachidonic acid (ARASCO® Martek, USA), and 2 g/100 g diet docosahexaenoic acid (DHASCO® Martek, USA). The control diet contained fresh MRS instead of the probiotic in spent culture medium, lactose (Fluka, 61340) and an increased quantity of maltodextrin (Glucidex D12, Roquette Freres, France) instead of the prebiotic and increased amounts of cocoa butter and corn oil replacing the docosahexaenoic and arachidonic acids. Likewise, supplemented diets containing only one of the ingredients of the composition according to the invention contained the appropriate placebo ingredient.

TABLE 1

Composition of the diets.

| Ingredient | Control | Supplemented 1 | Supplemented 2 | Supplemented 3 | Supplemented 4 |
|---|---|---|---|---|---|
| K-caseinate (g) | 20.00 | 20.00 | 20.00 | 20.00 | 20.00 |
| Corn starch (g) | 32.95 | 32.95 | 32.95 | 32.95 | 32.95 |
| Maltodextrin (g) | 20.74 | 12.58 | 12.58 | 12.58 | 12.58 |
| Sucrose (g) | 10.00 | 10.00 | 10.00 | 10.00 | 10.00 |
| Lactose (g) | 4.26 | | | | |
| Raftiline HP (g) | | 0.42 | | | 0.42 |
| Vivinal GOS 10 (g) | | 12.00 | | | 12.00 |
| Fat mix (g) (see below) | 7.00 | 7.00 | 7.00 | 7.00 | 7.00 |
| Mineral mix (AIN-93-G) | 3.50 | 3.50 | 3.50 | 3.50 | 3.50 |

TABLE 1-continued

Composition of the diets.

| Ingredient | Control | Supplemented 1 | Supplemented 2 | Supplemented 3 | Supplemented 4 |
|---|---|---|---|---|---|
| Vitamin mix (AIN-93-VX) | 1.00 | 1.00 | 1.00 | 1.00 | 1.00 |
| L-Cysteine (g) | 0.30 | 0.30 | 0.30 | 0.30 | 0.30 |
| Cholinhydrogen Tartrate DAB 10 | 0.25 | 0.25 | 0.25 | 0.25 | 0.25 |
| MRS (ml) | 0.80 | | 0.80 | | 0.80 |
| *L. paracasei* CNCM I 2116 (ml) | | 0.80 | | 0.80 | |

TABLE 2

Fat Mix

| Ingredient (g/100 g fat mix) | Control | Supplemented 1 | Supplemented 2 | Supplemented 3 | Supplemented 4 |
|---|---|---|---|---|---|
| Soybean oil | 25.12 | 26.44 | 26.44 | 25.12 | 25.12 |
| Trisun 80 | | 2.59 | 2.59 | | |
| Cocoa butter | 30.26 | 27.12 | 27.12 | 30.26 | 30.26 |
| Corn oil | 44.63 | 34.22 | 34.22 | 44.63 | 44.63 |
| ARASCO | | 4.70 | 4.70 | | |
| DHASCO | | 4.93 | 4.93 | | |

Statistics

Data are expressed as mean ±SEM. The normality and homoscedasticity of the data were checked in each group. Body weight from PND15 to PND21, body mass index and fat pad weight data were compared by one way ANOVA followed by Fisher Least Significant Difference (LSD) to assess the differences between the groups at every age. Body weight and intake curves from PND21 were compared by repeated measures ANOVA and LSD to assess the differences between the groups.

Results

Figure 2:
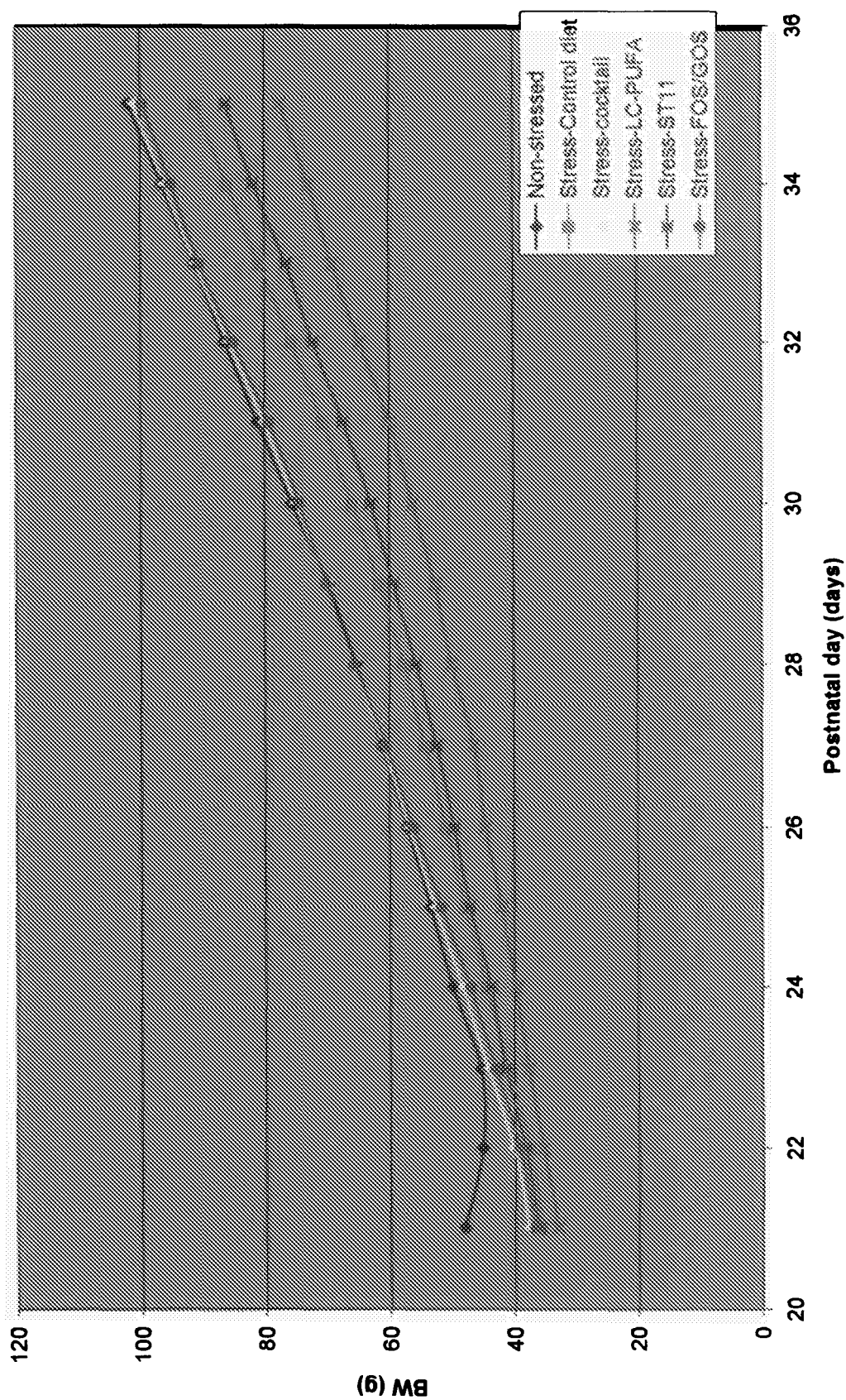
FIG. 2 shows the evolution of the body weight of the same groups of rats as in FIG. 1 from PND 21-36
Figure 3:
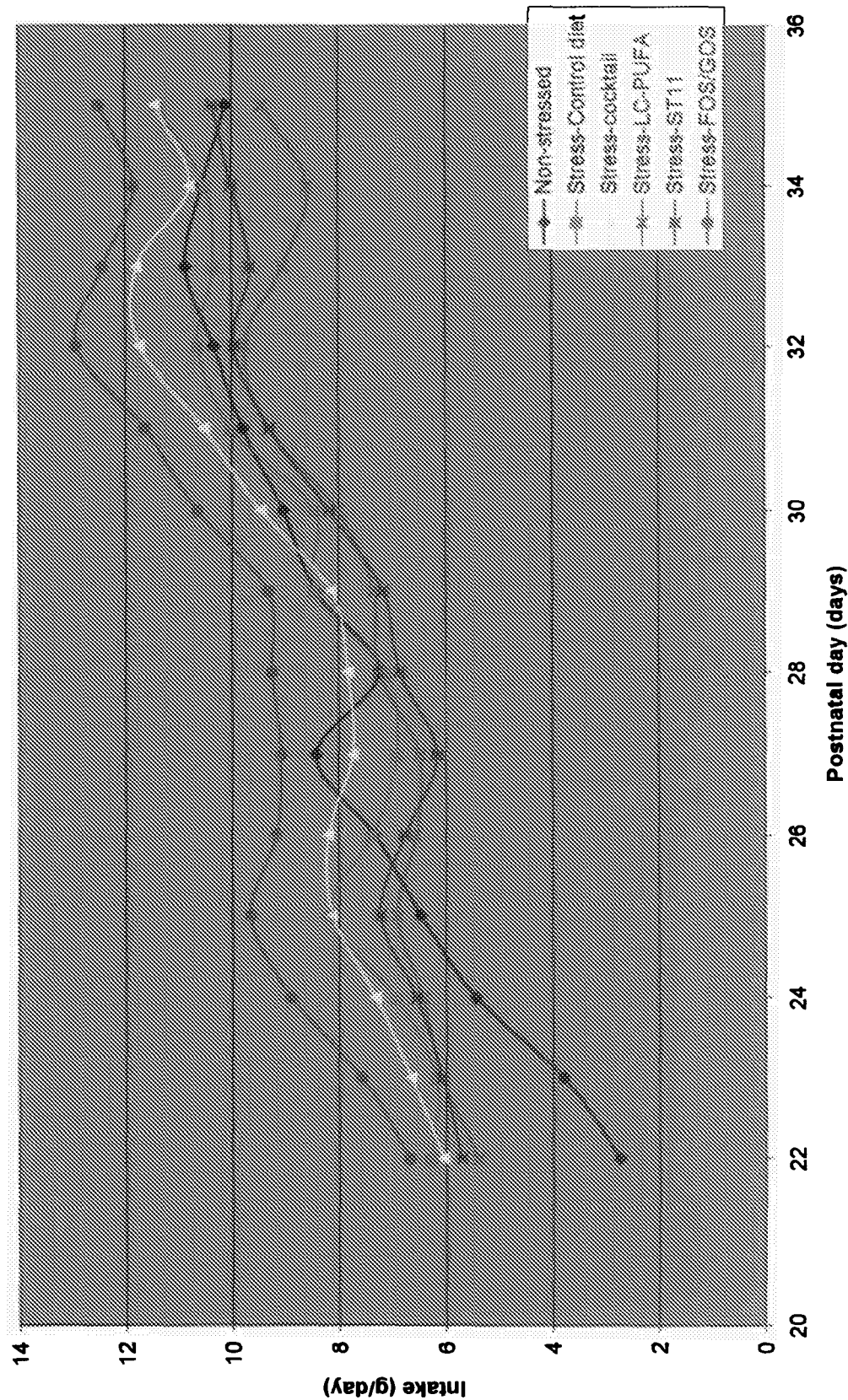
FIG. 3 shows the food intake of the same groups of rats from PND 21-36

The results are shown in the Figures. As may be seen from FIG. 1, the pups in the NS group continued to grow normally between PND 15 and 21 whilst all 5 MS groups lost weight until PND 17 and then resumed growth with the group fed the composition according to the invention (Supplemented Diet 1) exhibiting the most efficient catch-up growth. From PND 21 to 36, this trend accelerated with the group receiving the composition according to the invention achieving very similar weight at PND 36 as the NS group (FIG. 2). By comparison, it may be seen that the MS group fed the control diet (i.e. the same diet as the NS group) achieved a significantly lower body weight by PND 36. It may also be seen from FIG. 2 that the MS group receiving Supplemented Diet 4 (prebiotic only) also achieved a final weight comparable to that of the control NS group. The reason for this may be seen from FIG. 3 which shows that the food intake in this group was consistently higher from PND 21 to 36 than all the other groups. This higher calorific intake does not however seem to translate directly into growth. By comparison, the MS group receiving Supplemented Diet 1 had a lower food intake than the MS group receiving Supplemented Diet 4 and a comparable food intake with the other groups including the control diet.

Figure 4:
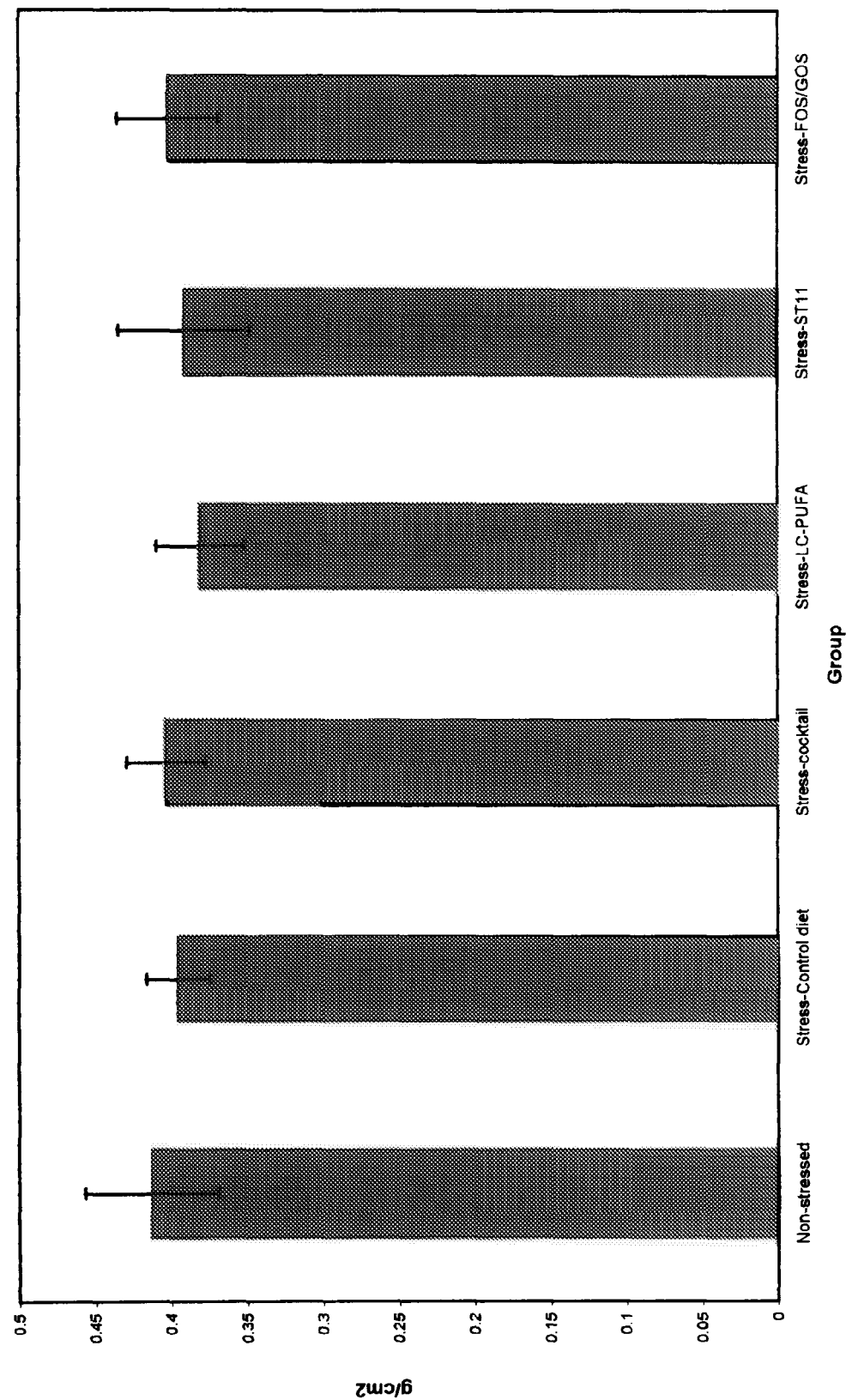
FIG. 4 shows the body mass indices in $g/cm^2$ for the six groups of rats at PND 36
Figure 5:
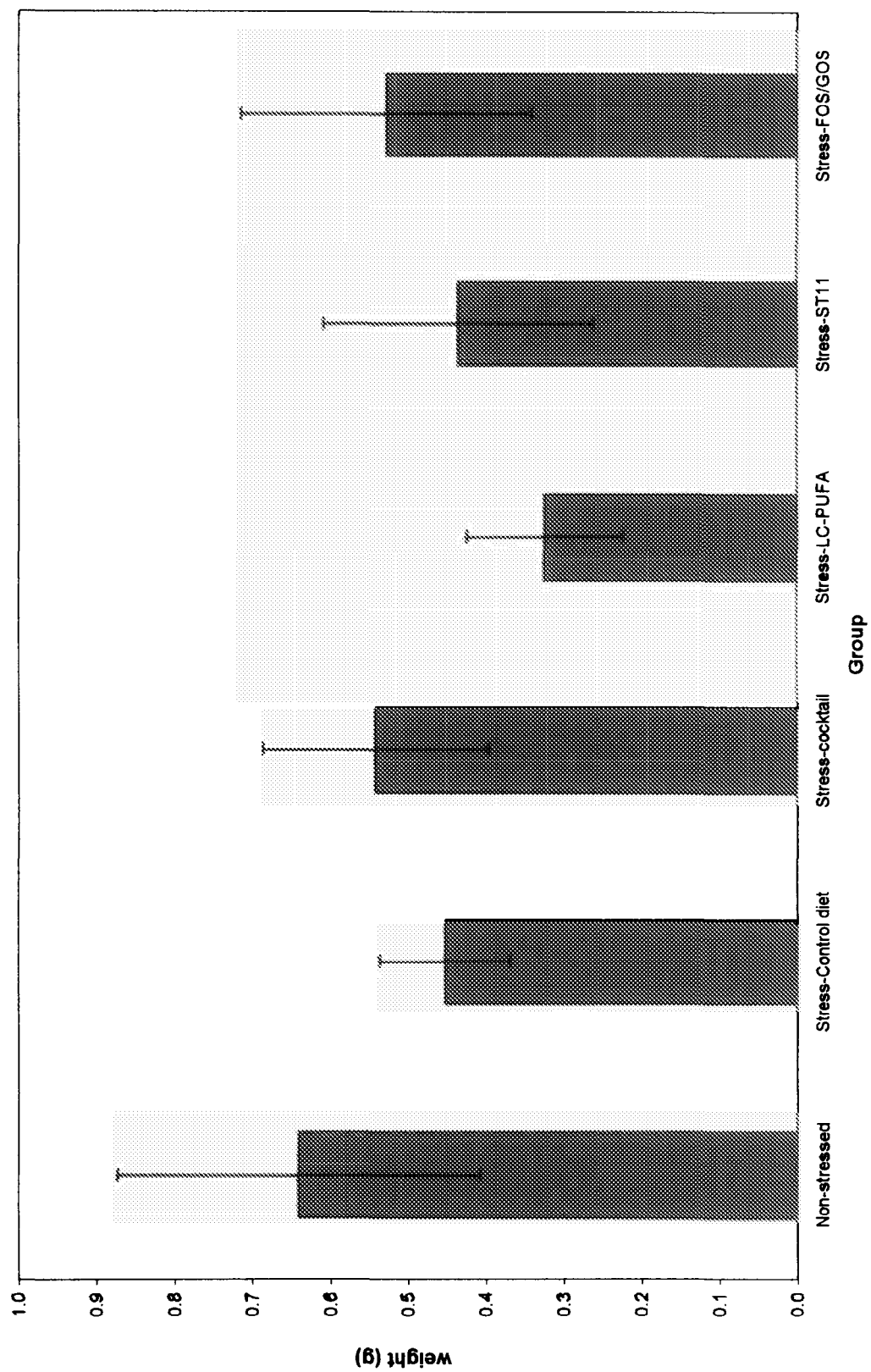
FIG. 5 shows the weight in g of the epididimal and retroperitoneal fat pads of the six groups of rats at PND 36

Further, it may be seen from FIGS. 4 and 5 that the catch up growth exhibited by the MS group receiving Supplemented Diet 1 was not associated with an increase in body mass index or total body fat mass as these parameters are comparable with those for the non-stressed group. We concluded that a nutritional formulation containing a combination of ingredients according to the present invention is effective in promoting catch-up growth in young mammals whose growth has been retarded due to physical or mental stress and that the combination is synergistic because the sum of the effects of the ingredients given individually is less than that of the combination. Further, the catch up growth is not associated with a disproportionate increase in body mass index and thus should not increase the risk of obesity in later life.

The invention claimed is:

1. A nutritional formulation comprising a source of lipids comprising fatty acids, an n3 long-chain polyunsaturated fatty acid (LC-PUFA) and an n6 LC-PUFA, each in an amount of at least 0.01% of the fatty acids in the formulation with a ratio of the n6 LC-PUFA to the n3 LC-PUFA ranging from 4:1 to 8:1, a prebiotic fibre in an amount of from 0.0001 to 0.05 g/g of the formulation and a probiotic bacterial strain in an amount of from $10^3$-$10^{11}$ cfu/g of the formulation, wherein the prebiotic fibre is selected from the group consisting of 1) a mixture having from 40 to 60% gum Arabic, from 10 to 20% inulin and from 30 to 40% fructo-oligosaccharide, and 2) a mixture having from 70 to 95% galacto-oligosaccharide and 5 to 30% fructo-oligosaccharide.

2. A formulation according to claim 1, wherein the probiotic bacterial strain is a *Lactobacillus*.

3. A formulation according to claim 2, wherein the *Lactobacillus* is *Lactobacillus paracasei* CNCM I-2116.

4. A formulation according to claim 1, wherein the prebiotic fibre is present in an amount of from 0.02 to 0.05 g/g of the formulation.

5. A formulation according to claim 1, wherein the n3 LC-PUFA is docosahexanoic acid.

6. A formulation according to claim 1, wherein the formulation is a pediatric nutritional formulation.

7. A method for promoting catch up growth in sick and convalescent young mammals, the method comprising:
administering to a sick and convalescent young mammal a composition comprising an n3 long-chain polyunsaturated fatty acid (LC-PUFA) and an n6 LC-PUFA with a ratio of the n6 LC-PUFA to the n3 LC-PUFA ranging from 4:1 to 8:1, a prebiotic fibre and a probiotic bacterial strain, wherein the prebiotic fibre is selected from the group consisting of 1) a mixture having from 40 to 60% gum Arabic, from 10 to 20% inulin and from 30 to 40% fructo-oligosaccharide, and 2) a mixture having from 70 to 95% galacto-oligosaccharide and 5 to 30% fructo-oligosaccharide.

8. The method of claim 7 wherein the composition comprises a source of lipids containing fatty acids and the n3 LC-PUFA is present in an amount of at least 0.01% of the fatty acids in a lipid source.

9. The method of claim 7, wherein the n6 LC-PUFA is present in an amount of at least 0.01% of the fatty acids of a lipid source.

10. The method of claim 7 wherein the prebiotic fibre is present in an amount of from 0.0001 to 0.05 g/g of the composition.

11. The method of claim 7 wherein the probiotic bacterial strain is present in an amount of from $10^3$-$10^{11}$ cfu/g of the composition.

12. The method of claim 7, wherein the probiotic bacterial strain is a *Lactobacillus*.

13. The method of claim 12, wherein the *Lactobacillus* is *Lactobacillus paracasei* CNCM I-2116.

14. The method of claim 7, wherein the prebiotic fibre is present in an amount of from 0.02 to 0.05 g/g of formulation.

15. The method of claim 7, wherein the prebiotic is a mixture of from 40 to 60% gum Arabic, from 10 to 20% inulin and from 30 to 40% fructo-oligosaccharide.

16. The method of claim 7, wherein the n3 LC-PUFA is docosahexanoic acid.

17. The method of claim 7, wherein the n6 LC-PUFA is arachidonic acid.

18. The method of claim 7, wherein the composition is a nutritional formulation.

19. The method of claim 7, wherein the composition is a medicament.

* * * * *